United States Patent [19]
Mikitenko et al.

[11] Patent Number: 6,060,634
[45] Date of Patent: *May 9, 2000

[54] PRODUCTION OF PARA-XYLENE FROM AN EFFLUENT FROM PARASELECTIVE TOLUENE DISPROPORTIONATION USING A CRYSTALLIZATION PROCESS COMBINED WITH SIMULATED MOVING BED ADSORPTION

[75] Inventors: Paul Mikitenko, Noisy le Roy; Gérard Hotier, Rueil Malmaison, both of France

[73] Assignee: Institut Francais du Petrole, France

[*] Notice: This patent is subject to a terminal disclaimer.

[21] Appl. No.: 09/132,771

[22] Filed: Aug. 12, 1998

Related U.S. Application Data

[62] Division of application No. 08/721,452, Jul. 27, 1996, Pat. No. 5,866,740.

[30] Foreign Application Priority Data

Sep. 29, 1995 [FR] France .................................. 95 11489

[51] Int. Cl.[7] .................. C07C 7/00; C07C 7/14; C07C 7/12; C07C 5/22

[52] U.S. Cl. .................. 585/814; 585/828; 585/812; 585/805; 585/470

[58] Field of Search .................. 585/814, 812, 585/805, 828, 475, 470

[56] References Cited

U.S. PATENT DOCUMENTS

| | | | |
|---|---|---|---|
| 3,548,017 | 12/1970 | Hebert et al. | 260/668 |
| 3,699,181 | 10/1972 | Kmecak et al. | 260/672 T |
| 3,729,523 | 4/1973 | Grandio et al. | 260/674 A |
| 3,813,452 | 5/1974 | Bieser | 260/674 SA |
| 3,916,018 | 10/1975 | Edison et al. | 260/674 A |
| 3,939,221 | 2/1976 | Pearce | 260/674 SA |
| 3,948,758 | 4/1976 | Bonacci et al. | 208/92 |
| 3,959,978 | 6/1976 | Lindley et al. | 62/58 |
| 4,118,429 | 10/1978 | Fritsch | 260/674 A |
| 4,402,832 | 9/1983 | Gerhold | 210/659 |
| 4,498,991 | 2/1985 | Oroskar | 210/659 |
| 4,940,830 | 7/1990 | Zinnen et al. | 585/828 |
| 4,948,758 | 8/1990 | Beall et al. | 501/3 |
| 5,173,461 | 12/1992 | Absil et al. | 502/62 |
| 5,284,992 | 2/1994 | Hotier et al. | 585/805 |
| 5,329,060 | 7/1994 | Swift | 585/805 |
| 5,629,467 | 5/1997 | Hotier et al. | 585/805 |
| 5,866,740 | 2/1999 | Mikitenko et al. | 585/470 |

FOREIGN PATENT DOCUMENTS

| | | |
|---|---|---|
| 531191 | 3/1993 | European Pat. Off. . |
| 2436076 | 2/1975 | Germany . |
| 003622 | 8/1979 | Germany . |
| 55-139327 | 1/1980 | Japan . |
| 1420796 | 1/1976 | United Kingdom . |

OTHER PUBLICATIONS

Patent Abstracts of Japan, vol. 5, No. 12 (C–40)(684) Jan. 24, 1981 and JP–A–55 139 327 Oct. 31, 1980.

*Primary Examiner*—Walter D. Griffin
*Assistant Examiner*—Thuan D. Dang
*Attorney, Agent, or Firm*—Millen White, Zelan & Branigan, P.C.

[57] ABSTRACT

Para-xylene is produced from a paraselective toluene disproportionation reactor, effluent (3) is distilled to eliminate toluene and benzene in at least 2 distillation columns (C1), (C2), and the xylenes (8) are crystallized at least once (10) at between +10° C. and –30° C. The separated mother liquor (14) is adsorbed on a zeolitic sieve in the presence of toluene in a simulated moving bed (15). This latter produces a raffinate (16) containing toluene which is depleted in para-xylene which is distilled in a distillation column (C4), and an extract which is enriched in para-xylene and contains toluene, which is recycled to columns (C1, C2). The para-xylene crystals are purified by washing with toluene and distillation or by partial melting (30) followed by washing with molten high purity para-xylene.

23 Claims, 4 Drawing Sheets

PRODUCTION OF PARA-XYLENE FROM AN EFFLUENT FROM PARASELECTIVE TOLUENE DISPROPORTIONATION USING A CRYSTALLIZATION PROCESS COMBINED WITH SIMULATED MOVING BED ADSORPTION

This is application is a divisional application of U.S. patent application Ser. No. 08/721,452, filed Sep. 27, 1996, now allowed as U.S. Pat. No. 5,866,740, issued Feb. 2, 1999.

BACKGROUND OF THE INVENTION

The present invention concerns a process for the production and improved separation of aromatic C8 hydrocarbons from a feed which is rich in para-xylene, such as a C8 cut from the Mobil toluene disproportionation process.

It has long been recognized that certain zeolitic materials catalyst certain hydrocarbon conversions as described, for example, in United States patent U.S. Pat. No. Particular hydrocarbon conversions which have been claimed are alkylation, transalkylation and disproportionation. Toluene disproportionation is claimed, for example, in United States patents U.S. Pat. No. 4,052,476; U.S. Pat. Nos. 4,007,231; 4,011,276; 4,016,219 and 4,029,761.

In their article in Oil and Gas Journal vol. 69, No 48 (1971), Grandio et aL describe a process for the disproportionation of toluene in the liquid phase using zeolitic catalysts in the absence of hydrogen.

It should be noted that in the first known processes, the composition of the xylenes obtained corresponds to the thermodynamic equilibrium at the operating temperature, namely 20% to 25% of p-xylene of the total of xylenes and ethylbenzene.

More recent patents, for example U.S. Pat. No. 4,380,685, describe alkylation, transalkylation and paraselective disproportionation of substituted aromatic compounds to form dialkylbenzenes. In the case of toluene disproportionation, the p-xylene concentration in the effluent produced exceeds the thermodynamic equilibrium. The catalyst used is based on zeolites characterized by a constraint index of 1 to 12, a silica/alumina ratio of at least 12/1 and comprising various metals and phosphorous; examples of the zeolites used are ZSM5, ZSM11, ZSM12 and ZSM35. Further, those catalysts must be treated to restrict diffusion of ortho- and meta-xylene through the pores of the crystal and to reduce re-isomerization of the p-xylene formed. This treatment essentially consists of precoking under well defined conditions which may be accompanied by addition of a small quantity of an oxide which is difficult to reduce (antimony, phosphorous, boron or magnesium), or by a surface treatment. Examples of methods for the preparation of such an effective catalyst are described in U.S. Pat. No. 5,173,461.

The process using those catalysts, termed the MSTDP process, has been described in two publications:

Selective toluene disproportionation process proven at Italian refinery, Gorra F., Breckenridge L. L., Guy W. M., Sailor R. A., Oil and Gas Journal Vol. 90, No. 41, 60–67 (1992) and in "Mobil's toluene to PX process proves itself", Mobil Research and Development Corp., European Chemical News Vol. 54, No 1418 (1990).

These publications describe the production of xylenes containing 80–95% of p-xylene for a conversion of 30% of toluene per pass.

A number of patents claim this process and describe catalyst preparations. Examples are European patent EP 26,962, U.S. Pat. Nos. 4,260,843; 4,274,982; 4,908,342; 5,173,461; and WO 93/17987.

In all cases, the disproportionation effluent has a simplified composition of close to: 70% toluene—15% benzene—15% xylenes. The composition of the xylene fraction is 85% p-xylene, 15% o-+m-xylene and ethylbenzene.

The present invention relates to an improved process for the separation of a C8 aromatic mixture to obtain p-xylene of sufficient purity for the production, for example, of terephthalic acid. One known method for the separation of p-xylene from a C8 aromatic cut consists of carrying out fractional crystallization; examples of existing processes are those or Chevron, Krupp, Amoco, Maruzen and Arco (U.S. Pat. No. 3,177,255 and U.S. Pat. No. 3,467,724). Those processes use the following procedure: the feed containing at least 20% of p-xylene is cooled to between 50° C. and 70° C. to cause crystallization, the crystals containing 85% to 90% of p-xylene and the mother liquors, 7% to 8%; the crystals are melted again and recrystallised at 10° C. After filtering the crystals and washing with toluene, for example, 99.5% pure p-xylene is obtained.

A further method for the separation of p-xylene from an aromatic C8 mixture is the liquid chromatographic method termed a simulated counter-current method claimed in U.S. Pat. No. 2,985,589 which uses zeolites to selectively adsorb the p-xylene. The Parex and Aromax processes use this method or a simulated co-current method (U.S. Pat. No. 4,402,832.

The advantages and disadvantages of those processes have been widely studied and described for different cases.

The prior art is also illustrated in U.S. Pat. No. 5,329,060 and EP-A-0 531 191 which describe a combination of adsorption, crystallization and isomerization steps for aromatic C8 cuts to produce very high purity para-xylene.

The peculiarity of the mixture obtained at the outlet from the paraselective disproportionation reactor in the MSTDP, after separation of the lighter hydrocarbons by distillation, is that it is particularly rich in p-xylene as it contains 75% to 85% of p-xylene.

This mixture can be treated in different ways:

1. High temperature crystallization

This means a temperature which is, for example, in the range +10° C. to −25° C. The yield of pure p-xylene is close to 83% when the concentration of p-xylene in the C8 cut in the effluent is 80 weight %. This yield is limited by the fact that the mother liquor still contains more than 40% of para-xylene due to the liquid-solid thermodynamic equilibrium.

2. Two-temperature crystallization

In this case, a first crystallization at a temperature in the range +10° C. to −25° C. leads to the production of pure para-xylene, the mother liquor is recrystallized at a lower temperature (−50° C. to −70° C.), the p-xylene-rich crystals are recycled to the feed to the first crystallization, the mother liquor from the second crystallization contains no more than about 10 weight % of p-xylene.

The global yield of para-xylene from the two-stage crystallization method for an initial feed of 80 weight % of para-xylene is about 97 weight %.

The disadvantage of this process is high energy consumption.

SUMMARY OF THE INVENTION

The aim of the present invention is to overcome the disadvantages described above.

More precisely, the invention concerns a process for the preparation of para-xylene from a toluene feed, comprising:

a) a paraselective toluene disproportionation step in the presence of hydrogen and a catalyst in a disproportionation zone to produce an effluent containing benzene, toluene, para-xylene enriched xylenes, ethylbenzene and aromatic hydrocarbons containing at least 9 carbon atoms;

b) an effluent distillation step using at least two distillation columns to separately produce benzene, toluene and xylenes;

c) a high temperature xylene crystallization step, preferably in the range +10° C. to −30° C., using at least one crystallization zone to produce very high purity para-xylene and a mother liquor which is depleted in para-xylene, the process being characterized in that:

d) the mother liquor is brought into contact with a zeolitic adsorption bed in a simulated moving bed adsorption zone in the presence of a toluene desorbent under conditions such that a first fraction is obtained which is depleted in para-xylene and contains toluene and a second fraction is obtained which is enriched in para-xylene and contains toluene;

e) at least a portion of the second fraction is recycled to the crystallization zone after distilling substantially all of the toluene.

The term "high temperature crystallization" means crystallization, in at least one crystallizer for each crystallization step, of a solution or suspension of para-xylene which is already enriched in para-xylene, corresponding to that termed a purification step in the literature. As an example, U.S. Pat. No. 2,866,833, which is hereby incorporated by reference, mentions a high temperature para-xylene purification step which can reach a temperature of −34° C.

Distillation step (b) can comprise distillation of the effluent from step (a) in a first distillation column (C1) to produce a distillate containing benzene and a first residue, distillation of the first residue in a second distillation column (C2) to produce a distillate containing toluene and a second residue, and distillation of the second residue in a third distillation column (C3) to produce a distillate containing xylenes and a third residue containing aromatic hydrocarbons containing at least 9 carbon atoms and in which at least a portion of the second fraction is distilled in the second distillation column (C2).

The third residue can be distilled to obtain a distillate containing ortho-xylene and a residue containing hydrocarbons containing at least 9 carbon atoms.

In a variation, distillation step (b) comprises distillation of the effluent from step (a) in a first distillation column (C1) to produce a distillate (BT) containing benzene and toluene and a residue containing xylenes and hydrocarbons containing at least 9 carbon atoms, the residue undergoes crystallization step (c), at least a portion of the second para-xylene enriched fraction is distilled in distillation column (C1), and distillate (BT) containing benzene and toluene is distilled in a distillation column (C2) to recover benzene as the distillate and toluene as the residue, and in which at least a portion of distillate (BT) from column (C1) is used to supply necessary heat to the reboiler for column (C2).

The residue from column (C1) containing xylenes, ethylbenzene and hydrocarbons containing at least 9 carbon atoms can be sent directly to at least one crystallization zone, but the residue can also be distilled in a column (C3) to recover a distillate containing xylenes and ethylbenzene which undergoes crystallization step (c). The hydrocarbons containing at least 9 carbon atoms are eliminated as a residue.

As a secondary feature, at least a portion of the toluene from distillation column C2 can be recycled to the adsorption zone, the remaining portion being recycled to the paraselective disproportionation zone.

In a first feature pertaining to adsorption, the first fraction which is depleted in para-xylene, containing toluene and the other aromatic hydrocarbons containing 8 carbon atoms and more, is distilled in a distillation column (C4) to produce toluene as a distillate, at least a portion of which is recycled to the adsorption zone, and a residue which is substantially free of toluene containing the first fraction, namely ortho-xylene, meta-xylene and ethylbenzene and possibly hydrocarbons containing at least 9 carbon atoms.

When the hydrocarbons containing at least 9 carbon atoms have not been eliminated upstream of the crystallization zone, they can be extracted as a residue in a distillation column (C3) downstream of column (C4).

In a second particularly advantageous feature pertaining to adsorption, at least a portion of the second para-xylene-enriched fraction containing toluene is recycled to distillation column (C1) when benzene alone is recovered as a distillate from column (C2). In a further variation, the second fraction is recycled to column (C2) when benzene alone is recovered as the distillate from column (C1).

There are a number of variations to the crystallization step for the xylenes after distillation with or without hydrocarbons containing at least 9 carbon atoms:

In a first variation, the xylenes are crystallized in accordance with step (c) in a crystallization zone to produce a suspension of para-xylene crystals in the mother liquor, the crystals are separated from the mother liquor in a separation zone, the crystals are washed with a suitable wash solvent, the mother liquor is recovered and sent to the adsorption zone in accordance with step (d) and very high purity para-xylene crystals are recovered, and the wash liquor is recovered and recycled to the distillation zone if the wash solvent contains toluene or to the crystallization zone or the adsorption zone if the wash solvent is molten para-xylene.

In a second variation which may be preferred with certain types of crystallizer, for example scraped surface crystallizers, the xylenes are crystallized in accordance with step (c) in at least two crystallization zones, one of which is at a colder temperature than the other, the mother liquor from the coldest crystallization zone being recovered and sent to the adsorption zone in accordance with step (d).

Whatever the variation, the para-xylene is crystallized at high temperature, as indicated above, for example between +10° C. and −34° C. and in particular between +10° C. and −25° C. More precisely, the lower temperature zone is at a temperature in the range 0° C. to −25° C. for example, while the higher temperature zone is at a temperature which is in the range +10° C. to −5° C., for example.

There are at least two variations to crystallization at two different temperatures:

In the first variation, the xylenes from the distillation step are crystallized in a first low temperature crystallization zone, the first para-xylene crystals are separated from a first mother liquor which is sent to the adsorption zone, the first crystals are melted, they are recrystallised in a second higher temperature crystallization zone, second para-xylene crystals are separated from a second mother liquor, washed with a suitable wash solvent, melted, and very high purity para-xylene is recovered, and at least a portion of the second mother liquor and optionally at least a portion of the wash liquor is recycled to the first crystallization zone and/or to the second crystallization zone and/or to the adsorption zone.

In a second variation, the xylenes from the distillation step are crystallized in a first high temperature crystallization zone, first para-xylene crystals are separated from a first mother liquor, the first mother liquor is recrystallized in a second lower temperature crystallization zone, second para-xylene crystals are separated from a second mother liquor which is sent to the adsorption zone, the first and second crystals are washed with a suitable wash solvent, melted, and very high purity para-xylene is recovered, and at least a portion of the wash liquor is recycled to the first crystallization zone or to the second crystallization zone and/or to the adsorption zone.

In a further implementation of the process, after having been crystallized and separated from its mother liquor, the para-xylene can be taken up again into suspension in a partial melting zone as described in French patent application FR 95/00746 which is hereby incorporated by reference.

In more detail, in a first variation the xylenes from the distillation step are crystallized in accordance with crystallization step (c) in a crystallization zone to produce a suspension of para-xylene crystals in a mother liquor, the crystals are separated from the mother liquor, partially melted in a partial melting zone, a second suspension of crystals is recovered, the second suspension is separated and washed in a separation and washing zone using a wash solvent which is toluene or molten very high purity para-xylene, very high purity para-xylene is recovered which is optionally melted, and a wash liquor is recovered which is at least partially recycled to the crystallization zone and/or to the adsorption zone after optional distillation if the wash solvent is toluene.

In a second variation, the xylenes from the distillation step are crystallized in a first high temperature crystallization zone, first crystals of para-xylene are separated from a first mother liquor, the first mother liquor is recrystallised in a second lower temperature crystallization zone, second para-xylene crystals are separated from a second mother liquor which is sent to the adsorption zone, the first and second crystals are partially melted in at least one partial melting zone, a suspension of crystals is recovered, the suspension is separated and washed in a separation and washing zone with a wash solvent which is toluene or molten very high purity para-xylene, very high purity para-xylene is recovered and optionally melted and a wash liquor is recovered, and at least a portion of the wash liquor is recycled to the first and/or second crystallization zone after optional distillation if the wash solvent is toluene, and/or to the adsorption zone.

The remaining portion of the wash liquor which is not recycled to the crystallization or adsorption zone can be introduced to the partial melting zone where the crystals obtained, which are smaller in size, are taken up into suspension.

The mother liquor can be selectively adsorbed in a simulated moving bed containing at least 3 zones. It may be a simulated counter-current moving bed (U.S. Pat. No. 2,985,589) or a simulated co-current bed (U.S. Pat. No. 4,498,991 and U.S. Pat. No. 4,402,832), which are hereby incorporated by reference.

In a first variation, the adsorbent from the adsorption zone is an adsorbent which is selective for para-xylene. It is preferably a Y zbolite which is at least partially exchanged with barium and potassium as described in U.S. Pat. No. 3,894,109, hereby incorporated by reference, and U.S. Pat. No. 3,558,732 which describes toluene as the desorbent. In this variation, the recovered extract containing the para-xylene enriched fraction and the desorbent are recycled to the distillation step (C1 or C2) upstream of the crystallization step while the raffinate enriched in ortho- and meta-xylene and ethylbenzene and the desorbent are treated in a distillation unit (C4), the desorbent being recycled to the adsorption unit.

In a second variation, the adsorbent is selective for the fraction which is depleted in para-xylene and containing meta- and ortho-xylene and ethylbenzene, in accordance with United states patents U.S. Pat. Nos. 4,940,830 and 5,382,742, hereby incorporated by reference. In this variation, the raffinate containing para-xylene and the desorbent are recycled to the distillation unit upstream of the crystallization zone while the extract containing the other xylenes and ethylbenzene and the desorbent are treated in the distillation unit (C4), the desorbent then being recycled to the adsorption unit.

The prior art scheme comprising paraselective disproportionation of toluene and 1- or 2-stage crystallization requires crystallization at a very low temperature if a very high para-xylene yield is required, this being very expensive energy-wise. Apart from this, up to 3% by weight of para-xylene can be lost depending on the crystallization temperature used, with the inventive interposition of an adsorption step to treat the mother liquor recovered from crystallization, this very low temperature crystallization is avoided and para-xylene losses are limited to less than 0.1% by weight.

Further, using toluene as the desorbent means that it can be regenerated in one of the columns which treats the disproportionation effluent without the need to add a specific distillation column to separate para-xylene from the desorbent

BRIEF DESCRIPTION OF THE DRAWINGS

The invention will be better understood from the following figures which schematically illustrate a number of implementations of the process for the production of very high purity para-xylene. In the figures.

DETAILED DESCRIPTION OF THE DRAWINGS

Figure 1:
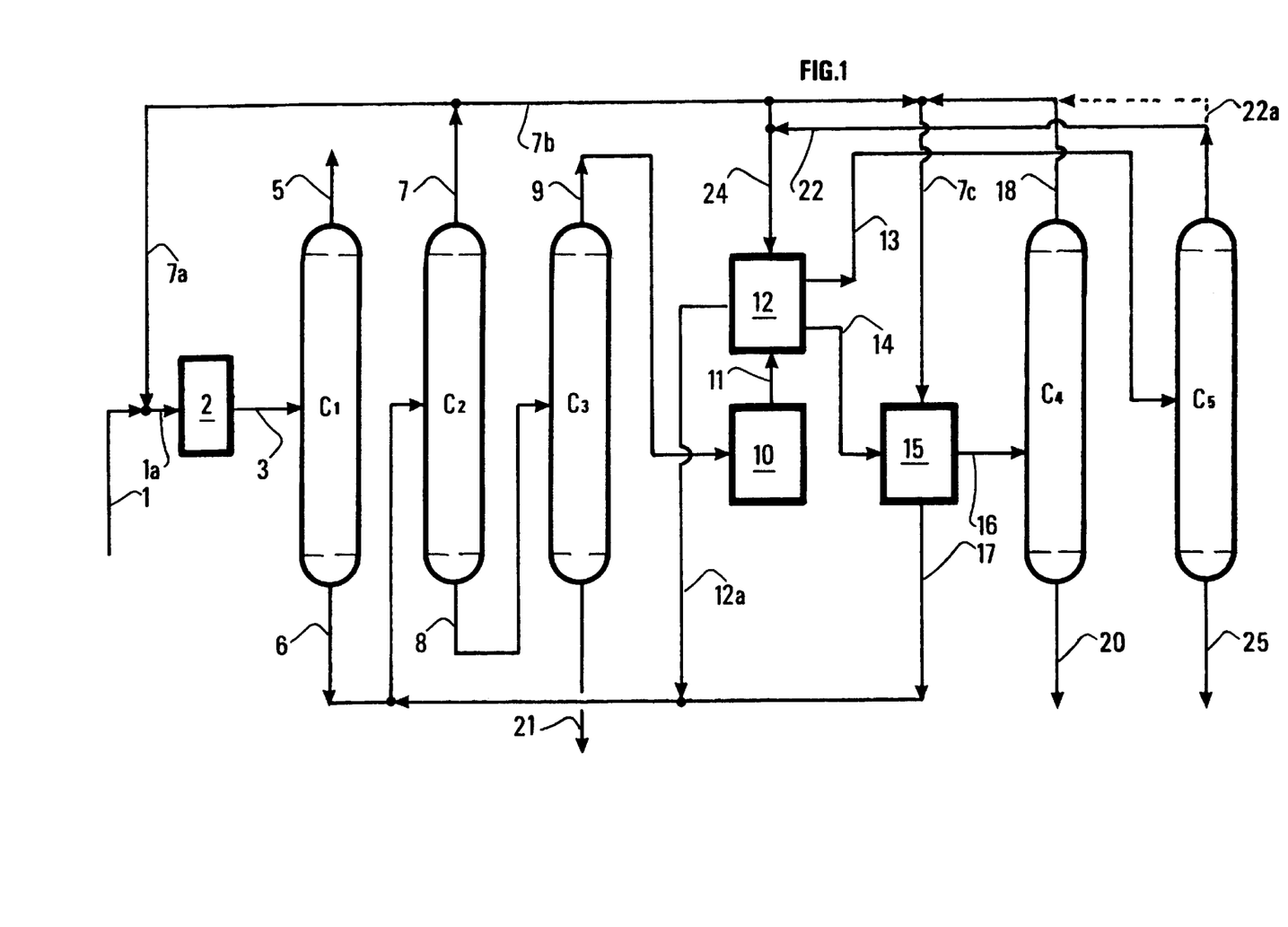
FIG. 1 shows the sequence of steps in the process: disproportionation, fractionation, crystallization and purification of para-xylene and adsorption of para-xylene from the mother liquor.

Toluene supplied via line 1a resulting from a line 1 and a recycling line 7a is introduced into a paraselective toluene disproportionation reactor 2 to produce benzene and xylenes, more particularly para-xylene.

An effluent is recovered, cooled and clay treated after separating hydrogen which is recycled and eliminating light hydrocarbons (not shown in the figure).

After this treatment the effluent from the reactor, containing about 15.5% by weight of xylenes and heavier hydrocarbons, of which 80% is para-xylene, 16.5% of benzene and 68% of unreacted toluene, is directed via a line 3 and introduced into a distillation column (C1) to produce a distillate constituted by benzene via a line 5 and a residue containing toluene, xylenes, ethylbenzene and hydrocarbons containing at least 9 carbon atoms (C9+) via a line 6. The residue supplies a distillation column (C2) from which toluene is partially extracted as a distillate via a line 7, a portion of which is recycled to reactor 2 via line 7a, while the other portion of the toluene is recovered via a line 7b for subsequent washing of para-xylene crystals or as a desorbent. Xylenes and hydrocarbons (C9+) are recovered from column (C2) as a residue via a line 8.

Line 8 supplies a distillation column (C3) which produces a C9+ residue via a line 21 and a distillate via a line 9 which essentially contains ortho- and meta-xylene, para-xylene and ethylbenzene.

This distillate is introduced via line 9 into a crystallization zone comprising at least one crystallizer operating at a temperature of +10° C. to −25° C., for example. Paraxylene crystals in suspension in a mother liquor which is depleted in para-xylene and contains meta-xylene and ethylbenzene are recovered via a line 11 and separated in a centrifuge 12. The crystals are washed in the centrifuge in the presence of a toluene wash solvent supplied via a line 24 connected to outlet line 7b from distillation column (C2). A wash liquor containing impurities and toluene is recycled via a line 12a towards distillation column (C2) to separate the toluene. Pure para-xylene crystals recovered from the centrifuge which still contain toluene are melted in a melter (not shown in the Figure) then introduced to a distillation column (C5) via line 13. A toluene distillate is recycled via a line 22 and line 24 to the washing apparatus of the centrifuge while very high purity para-xylene is extracted as the residue from column (C5) via a line 25.

The mother liquor recovered from centrifuge 12 which is depleted in para-xylene and also contains ethylbenzene, meta-xylene and ortho-xylene, is introduced via a line 14 into an adsorption zone 15 constituted by twelve beds of adsorbent and operating as a simulated counter-current bed as described in U.S. Pat. No. 5,284,992. The adsorbent is a Y zeolite exchanged with barium and potassium. Toluene, from distillation column (C2) via lines 7 and 7b, from the toluene purification column (C5) via line 22a and/or from distillation column (C4) described below via a line 18, is introduced into the adsorption zone as the eluent or desorption solvent via a line 7c. A raffinate containing toluene, depleted in para-xylene and enriched in meta- and/or ortho-xylene and in ethylbenzene is recovered via line 16. An extract containing toluene and enriched in para-xylene is desorbed and recycled via a line 17 to toluene distillation column (C2).

Figure 2:
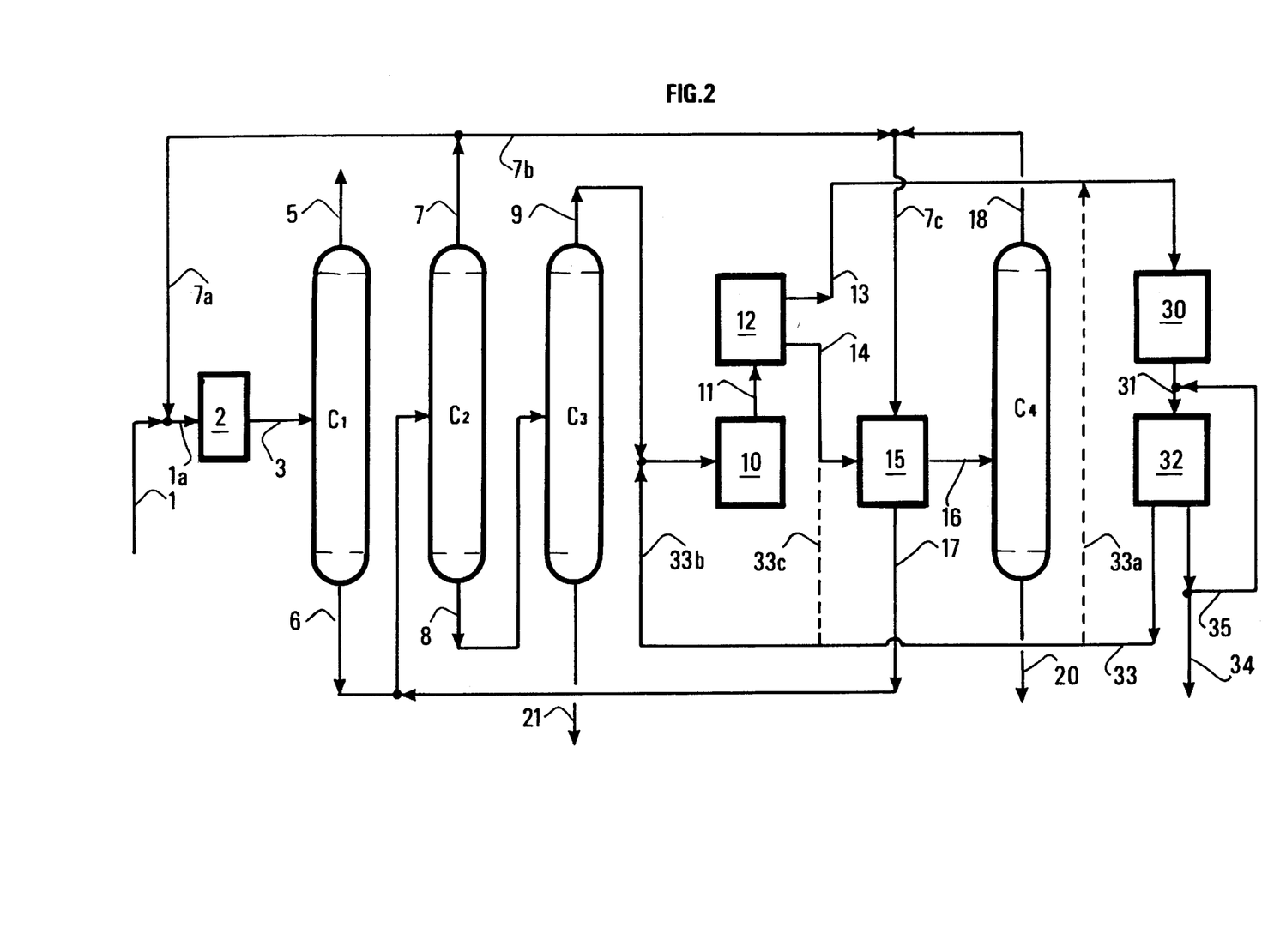
FIG. 2 shows a sequence with purification of para-xylene by washing with para-xylene preceded by taking the crystals up into suspension.

In FIG. 2, which uses the same reference numerals as FIG. 1 for the same means, the suspension of para-xylene crystals in the mother liquor from crystallization unit 10 is introduced via line 11 into centrifuge 12. The recovered mother liquor is treated as in FIG. 1 while the para-xylene crystals are taken up again into suspension in a partial melting zone to which they are introduced via line 13.

The new suspension recovered via line 31 is washed in a NIRO type counter-current washing column 32 as described, for example, in U.S. Pat. Nos. 4,475,355, 4,481,169, Swiss patent 515,730 and French patent application FR 95/00 746, using a portion of the very high purity para-xylene recovered from the column via a line 35. At least a portion of a wash liquor containing para-xylene is recovered via line 33 and recycled to crystallization zone 10 via line 33b and/or to adsorption zone 15 via a line 33c while the remaining portion can be introduced via a line 33a into line 13, thus facilitating taking the crystals up into suspension again and their transfer to partial melting zone 30. The wash liquor is preferably recycled to crystallization zone 10 and partial melting zone 30 because of the high para-xylene content.

Finally, very high purity para-xylene is recovered via a line 34.

Figure 3:
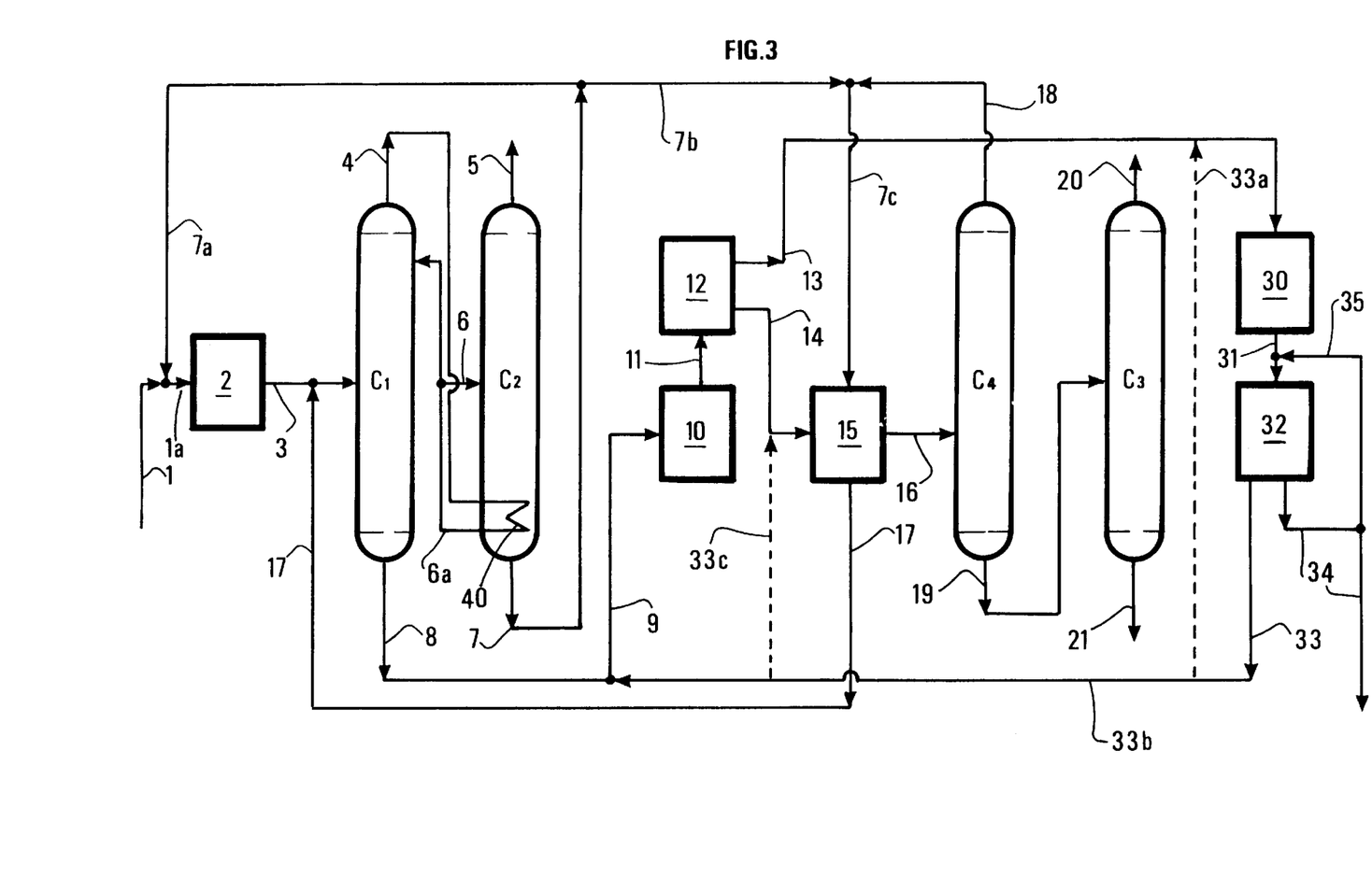
FIG. 3 shows a particular implementation of fractionation by distillation.

FIG. 3 shows a variation of the distillation step, the para-xylene crystallization step and the crystal purification step being the same as those of FIG. 1 or FIG. 2.

Means which are common to those in FIGS. 1 and 2 are given the same reference numerals.

A mixture 317 of effluent 3 from the paraselective toluene disproportionation reactor and the contents of a line 17 which is described below is distilled in a distillation column (C1) to produce a residue containing xylenes and hydrocarbons containing at least 9 carbon atoms which is sent to the crystallization zone via line 8. Column (C1) also produces a gaseous distillate containing benzene and toluene which is condensed and yields its heat of condensation to the reboiler of a distillation column (C2). After condensing, the distillate is partially recycled via a line 6a as a reflux to the head of column (C1), while the remaining portion supplies column (C2) via line 6. Benzene is recovered as a distillate via line 5 and toluene as a residue via lines 7, 7a which are connected to disproportionation reactor 2 and via lines 7 and 7b to adsorption columns 15 and/or to an apparatus for washing the separated crystals (line 24, FIG. 1).

The separated para-xylene crystals are sent as in FIG. 2 to the partial melting zone and purified as described with reference to FIG. 2.

The mother liquor from the centrifuging step is sent to adsorption columns 15. The resulting extract is recycled to distillation column (C1) via line 17 while the raffinate which is depleted in para-xylene but contains C9+ hydrocarbons is distilled in distillation column (C4) to eliminate substantially all the toluene (line 18). The residue, which also contains hydrocarbons containing at least 9 carbon atoms, is sent via a line 19 to a distillation column (C3) of reduced dimensions, from which the hydrocarbons are extracted as a residue via a line 21 and ortho- and meta-xylene and ethylbenzene are extracted as a distillate.

Figure 4:
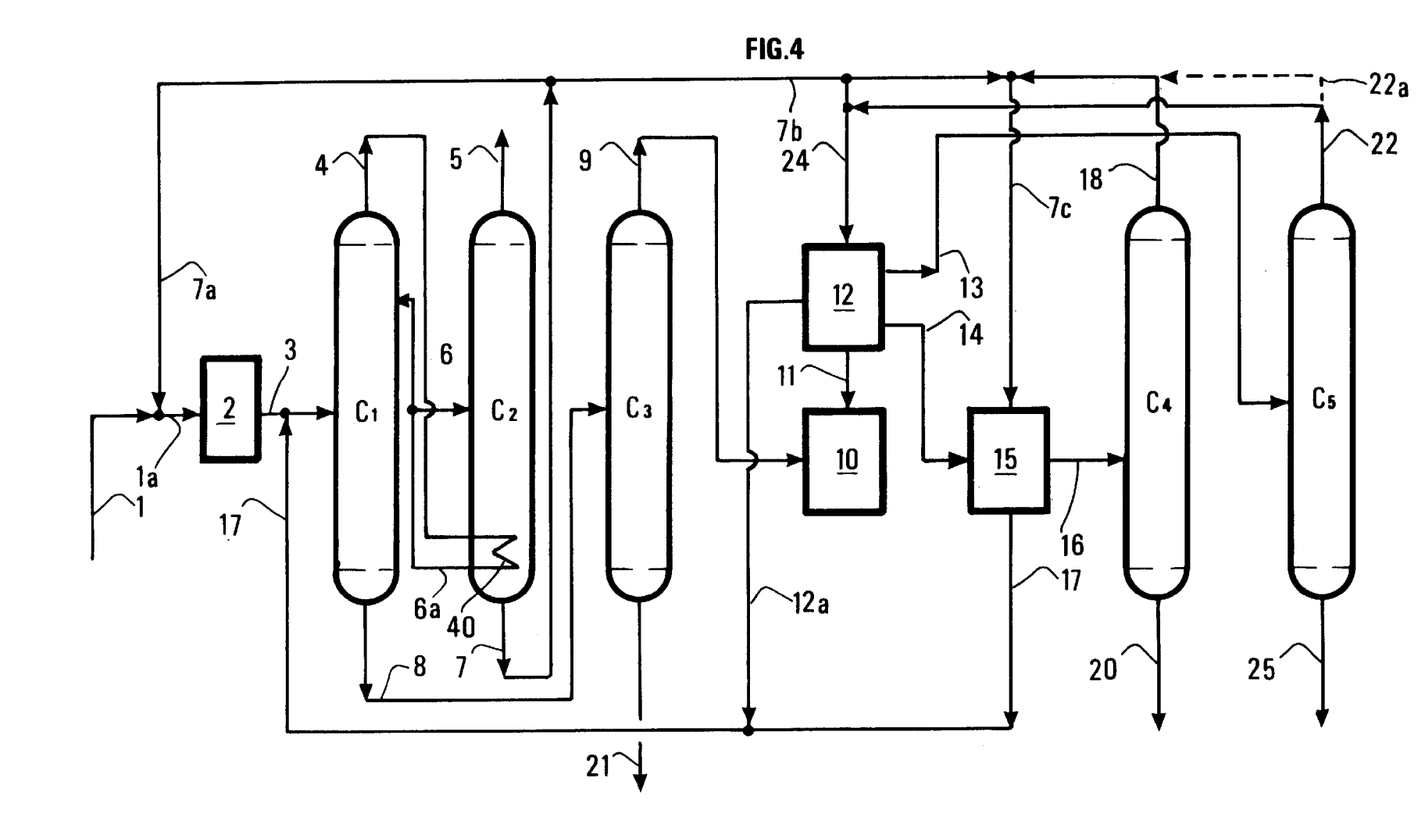
FIG. 4 shows fractionation by distillation which is identical to that of FIG. 3 but with prior separation of C9=hydrocarbons upstream of the crystallization step.

In FIG. 4, instead of removing the hydrocarbons containing at least 9 carbon atoms after the raffinate distillation step as in FIG. 3, they are extracted before the crystallization step. To this end, a distillation column (C3) with larger dimensions than that of FIG. 3 is supplied with the residue from column (C1) containing the xylenes and the hydrocarbons containing at least 9 carbon atoms. A residue containing only the hydrocarbons is recovered via line 21 and the xylenes are recovered via a line 9 then introduced into crystallization zone 10. Once separated from the mother liquor and washed, the para-xylene crystals are purified in column (C5) as described for FIG. 1, the toluene being recycled via line 22 to the centrifuge-washer. The resulting wash liquor is recycled via lines 12a and 17 to distillation column (C1).

The following example illustrates the invention.

Table 1 shows the material balance for the process described in respect of FIG. 3, the different lines using the reference numerals used in that Figure.

The operating conditions of the various steps are summarised below:

Paraselective dispropordonation reactor
(MSTDP from Mobil)

Catalyst: activated ZSM5
   $H_2$/hydrocarbons (molar): 1.5
   Temperature: 450° C.
   Pressure: 25 bar
   WSHV: 3.5

Distillation columns:

(C1): 70 plates; reflux 1.5
   (C2): 70 plates; reflux 2.5
   (C3): 70 plates; reflux 1.5
   (C4): 70 plates; reflux 1.5

Crystallizer

Temperature: −20° C. at atmospheric pressure
   Partial melting: 7C at atmospheric pressure
   Adsorption: simulated counter-current
      Sieve: Y zeolite, Ba and K exchanged
      Toluene/feed: 1.2
      Temperature: 150° C.
      Pressure: 10–15 bar
      Crystal wash: molten para-xylene Under these conditions, substantially all of the para-xylene produced in the disproportionation reactor was recovered with a purity of 99.9%.

TABLE 1

| | Total and partial mass flow rates in $g.h^{-1}$ | | | | | | | | | | | | |
|---|---|---|---|---|---|---|---|---|---|---|---|---|---|
| Line No | 1 | 3 | 5 | 6 | 7 | 7b | 7c | 14 | 16 | 20 | 33 | 33b | 34 |
| Benzene | | 1150 | 1150 | 1150 | | | | | | | | | |
| Toluene | 2225 | 4700 | <0.15 | 5067 | 5067 | 367 | 550 | 210 | 183 | | 1370 | 232 | 800 |
| pxylene | | 800 | | | | | | 210 | | | | | |
| (o + m)-xylene, EB | | 200 | | | | | | 223 | 200 | 200 | 230 | 38 | <1 |
| C9+ | | 75 | | | | | | 84 | 75 | | | | |
| aromatics | | | | | | | | | | | | | |
| Total | 2225 | 6925 | 1150 | 6217 | 5067 | 367 | 550 | 517 | 458 | 200 | 1600 | 270 | 800 |

We claim:

1. A process for the preparation of para-xylene from a toluene feed, comprising:
   a) paraselectively disproportionating toluene in the presence of hydrogen and a catalyst in a disproportionation zone to produce an effluent containing benzene, toluene, para-xylene enriched xylenes, ethylbenzene and aromatic hydrocarbons containing at least 9 carbon atoms;
   b) distilling the effluent of (a) using at least two distillation columns to separately produce benzene, toluene and xylenes;
   c) crystallizing the xylenes of (b) using at least one crystallization zone to produce very high purity para-xylene and a mother liquor which is depleted in paraxylene,
   d) contacting said mother liquor of (c) with a zeolitic adsorption bed in a simulated moving bed adsorption zone in the presence of a desorbent, under conditions such that a first fraction is obtained which is depleted in para-xylene and contains desorbent and a second fraction is obtained which is enriched in para-xylene and contains desorbent; and
   (e) recycling at least a portion of said second fraction to the crystallization zone after distilling substantially all of the desorbent.

2. A process according to claim 1, in which distillation (b) comprises distilling the effluent from (a) in a first distillation column (C1) to produce a distillate containing benzene and a first residue, distilling the first residue in a second distillation column (C2) to produce a distillate containing toluene and a second residue, and distilling the second residue in a third distillation column (C3) to produce a distillate containing xylenes and a third residue containing aromatic hydrocarbons containing at least 9 carbon atoms and in which at least a portion of said second fraction is distilled in the second distillation column (C2).

3. A process according to claim 2, in which the third residue is distilled to obtain a distillate containing ortho-xylene and a residue containing hydrocarbons containing at least 9 carbon atoms.

4. A process according to claim 1, in which distillation (b) comprises distilling the effluent from (a) in a first distillation column (C1) to produce a distillate (BT) containing benzene and toluene and a residue containing xylenes and hydrocarbons containing at least 9 carbon atoms, crystallizing said residue in (c), distilling at least a portion of said second para-xylene enriched fraction in distillation column (C1), and distilling a distillate (BT) containing benzene and toluene in a distillation column (C2) to recover benzene as the distillate and toluene as the residue, and in which at least a portion of distillate (BT) from column (C1) is used to supply heat to a reboiler for column (C2).

5. A process according to claim 4, in which at least a portion of the toluene from distillation column (C2) is recycled to the adsorption zone, the remaining portion being recycled to the disproportionation zone.

6. A process according to claim 4, in which the residue from column (C1) is distilled in a distillation column (C3) and a distillate containing xylenes is recovered which is subjected to crystallization (c), also a residue containing hydrocarbons containing at least 9 carbon atoms is recovered.

7. A process according to claim 2, in which the first fraction which is depleted in para-xylene, containing toluene, is distilled in a distillation column (C4) to produce toluene as a distillate, at least a portion of which is recycled to the adsorption zone, and a residue containing the first fraction which is substantially free of toluene.

8. A process according to claim 7, in which the residue from distillation column (C4) is distilled in a distillation column (C3) to obtain a distillate containing orthod-xylene, meta-xylene and ethylbenzene and a residue containing hydrocarbons containing at least 9 carbon atoms.

9. A process according to claim 2, in which at least a portion of the second fraction which is enriched in para-xylene and contains toluene is recycled to distillation column (C1).

10. A process according to claim 2, in which at least a portion of the second fraction which is enriched in para-xylene and contains toluene is recycled to column (C2).

11. A process according to claim 1, in which the xylenes are crystallized in accordance with (c) in the crystallization zone to produce a suspension of para-xylene crystals in the mother liquor, said crystals are separated from the mother liquor in a separation zone, the crystals are washed with a suitable wash solvent, the mother liquor is recovered and sent to the adsorption zone if the wash solvent is molten para-xylene.

12. A process according to claim 1, in which the xylenes are crystallized in accordance with (c) in at least two crystallization zones, one of which is at a colder temperature than the other, the mother liquor from the coldest crystallization zone being recovered and sent to the adsorption zone in accordance with (d).

13. A process according to claim 12, in which the xylenes are crystallized in a first low temperature crystallization zone, the first para-xylene crystals are separated from a first mother liquor which is sent to the adsorption zone, the first crystals are melted, and then recrystallized in a second higher temperature crystallization zone, second para-xylene crystals are separated from a second mother liquor, washed with a suitable wash solvent, melted and very high purity para-xylene is recovered, and at least a portion of the second mother liquor and optionally at least a portion of the wash liquor is recycled to the first crystallization zone and/or to the second crystallization zone and/or to the adsorption zone.

14. A process according to claim 12, in which the xylenes are crystallized in a first high temperature crystallization zone, first para-xylene crystals are separated from a first mother liquor, the first mother liquor is recrystallized in a second lower temperature crystallization zone, second para-xylene crystals are separated from a second mother liquor which is sent to the adsorption zone, the first and second crystals are washed with a suitable wash solvent, melted, and very high purity para-xylene is recovered, and at least a portion of the wash liquor is recycled to the first crystallization zone or to the second crystallization zone and/or to the adsorption zone.

15. A process according to claim 1, in which the xylenes are crystallized in accordance with crystallization (c) in a crystallization zone to produce a suspension of para-xylene crystals in a mother liquor, said crystals are separated from the mother liquor, partially melted in a partial melting zone, a second suspension of crystals is recovered, said second suspension is separated and washed in a separation and washing zone using a wash solvent which is toluene or molten very high purity para-xylene, very high purity para-xylene is recovered which is optionally melted, and a wash liquor is recovered which is at least partially recycled to the crystallization zone and/or to the adsorption zone after optional distillation if the wash solvent is toluene.

16. A process according to claim 1, in which the xylenes are crystallized in a first high temperature crystallization zone, first crystals of para-xylene are separated from a first mother liquor, the first mother liquor is recrystallized in a second lower temperature crystallization zone, second para-xylene crystals are separated form a second mother liquor which is sent to the adsorption zone, the first and second crystals are partially melted in at least one partial melting zone, a suspension of crystals is recovered, said suspension is separated and washed in a separation and washing zone with a wash solvent which is toluene or molten very high purity para-xylene, very high purity para-xylene is recovered and optionally melted and a wash liquor is recovered, and at least a portion of the wash liquor is recycled to the first and/or second crystallization zone after optional distillation if the wash solvent is toluene, and/or to the adsorption zone.

17. A process according to claim 15, in which the remaining portion of the wash liquor is recycled to the partial melting zone.

18. A process according to claim 11, in which the wash solvent is toluene, the very high purity para-xylene containing toluene is distilled in a distillation column and the toluene is recycled as the wash solvent.

19. A process according to claim 1, wherein the crystallization in (c) is conducted at +10° C. to −30° C.

20. A process according to claim 1, wherein the high purity para-xylene from (c) is brought into suspension in a partial remelting zone, and the suspension is washed in a countercurrent washing zone.

21. A process according to claim 20, wherein washing of the suspension is performed with very high purity para-xylene obtained from the washing zone.

22. A process for the preparation of paraxylene, comprising contacting a mother liquor, produced by high temperature crystallization of a xylene feed from paraselective toluene disproportionation, with a zeolitic adsorption bed in a simulated moving bed adsorption zone in the presence of a desorbent, whereby a first fraction depleted in paraxylene and a second fraction enriched in paraxylene is produced, and recycling at least a portion of the second fraction to crystallization.

23. A process according to claim 22, wherein the desorbent is toluene.

* * * * *